United States Patent [19]

Arai et al.

[11] Patent Number: 5,629,206

[45] Date of Patent: May 13, 1997

[54] METHOD OF CONTROLLING INSERTION SEQUENCE OF FILMS IN BIO-CHEMICAL ANALYSIS

[75] Inventors: Takaki Arai; Osamu Seshimoto, both of Saitama-ken, Japan

[73] Assignee: Fuji Photo Film Co., Ltd., Kanagawa-ken, Japan

[21] Appl. No.: 582,046

[22] Filed: Jan. 2, 1996

Related U.S. Application Data

[63] Continuation of Ser. No. 298,121, Aug. 30, 1994, abandoned.

[30] Foreign Application Priority Data

Sep. 14, 1993 [JP] Japan .................. 5-228413

[51] Int. Cl.⁶ .................................. G01N 33/52
[52] U.S. Cl. ...................... 436/46; 436/48; 436/50; 436/55; 422/63; 422/66; 422/67
[58] Field of Search ................... 436/43, 46–49, 436/174, 175, 805, 807, 50, 55; 422/63–67

[56] References Cited

U.S. PATENT DOCUMENTS

| | | |
|---|---|---|
| 4,303,611 | 12/1981 | Jessop ............................ 422/65 |
| 4,826,659 | 5/1989 | Akisada .......................... 422/63 |
| 4,855,109 | 8/1989 | Muraishi et al. ................ 422/63 |
| 4,871,679 | 10/1989 | Tanaka et al. . |
| 4,966,784 | 10/1990 | Tanaka et al. . |
| 5,049,359 | 9/1991 | Azuma et al. .................. 422/67 |
| 5,075,079 | 12/1991 | Kerr et al. ...................... 422/64 |
| 5,081,038 | 1/1992 | Sugaya et al. .................. 436/46 |
| 5,139,743 | 8/1992 | Ishizaka et al. ................ 422/63 |
| 5,244,632 | 9/1993 | Shaw et al. ..................... 422/63 |

FOREIGN PATENT DOCUMENTS 2-247563  10/1989  Japan .

Primary Examiner—Long V. Le
Attorney, Agent, or Firm—McAulay Fisher Nissen Goldberg & Kiel, LLP

[57] ABSTRACT

A dry chemical analysis film deposited with a sample liquid is inserted into an incubator to be incubated at a predetermined temperature, a coloring reaction of the chemical analysis film is measured after the incubation and then the chemical analysis film is discharged from the incubator. A plurality of chemical analysis films are subjected to these steps one by one after the preceding chemical analysis film is discharged from the incubator. When a first chemical analysis film is for an analyte which generates an interfering gas or the like which can adversely affects the accuracy of measurement of other chemical analysis films and a second chemical analysis film the accuracy of measurement on which can be adversely affected by the interfering gas or the like is to be inserted into the incubator after the first chemical analysis film is discharged, an adsorptive film which adsorbs the interfering gas or the like generated from the first chemical analysis film is inserted into the incubator after discharge of the first chemical analysis film prior to insertion of the second chemical analysis film.

2 Claims, 2 Drawing Sheets

METHOD OF CONTROLLING INSERTION SEQUENCE OF FILMS IN BIO-CHEMICAL ANALYSIS

This is a continuation of application Ser. No. 08/298,121, filed Aug. 30, 1994, now abandoned.

BACKGROUND OF THE INVENTION

1. Field of the Invention

This invention relates to a method of biochemical analysis in which a sample liquid such as blood, urine or the like is deposited (or spotted) on a "dry-to-the-touch" chemical analysis film having thereon a reagent layer whose optical density changes by chemical reaction with a specific biochemical component contained in the sample liquid, the chemical analysis film deposited with the sample liquid is incubated at a constant temperature in an incubator and the concentration of the specific biochemical component in the sample liquid is determined by measuring the optical density of the chemical analysis film, and more particularly to a method of dealing with interfering substances which can be generated during incubation of one chemical analysis film and can adversely affect the accuracy of measurement on another chemical analysis film incubated after said one chemical analysis film.

2. Description of the Prior Art

There has been put into practice a dry chemical analysis film with which a specific component such as urea nitrogen, glucose, hemoglobin, ammonia or the like contained in a sample liquid such as blood, urine or the like can be quantitatively analyzed through a droplet of the sample liquid deposited on the film. When biochemical components or the like contained in a sample liquid is analyzed using such a dry chemical analysis film, a droplet of the sample liquid is deposited on the film and is held at a predetermined constant temperature for a predetermined time in an incubator so that coloring reaction (coloring matter forming reaction) occurs, and the optical density of the color formed by the coloring reaction is optically measured. That is, measuring light containing a wavelength which is preselected according to the combination of the component to be analyzed (an analyte; sometimes referred to as "a measuring item") and the reagent contained in the reagent layer of the film is projected onto the film and the optical density of the slide is measured. Then the component to be analyzed is quantitatively analyzed on the basis of the optical density using a standard curve (or a calibration curve) which represents the relation between the concentration (or the activity) of the biochemical component and the optical density.

The dry chemical analysis film generally comprises a base film of plastic or the like and a reagent layer formed thereon and is sometimes called a multi-layered analysis element. Further the dry chemical analysis film may comprise a porous material layer such as filter paper impregnated with a reagent. The chemical analysis film is generally used in the form of a slide where the chemical analysis film is mounted in a plastic frame though it is sometimes used without frame. In this specification, the term "chemical analysis film" should be interpreted to include both the chemical analysis slide and the frameless chemical analysis film. The chemical analysis films are transferred to the incubator one by one after deposition of the sample liquid and inserted into cells in the incubator. Each cell is in the form of a slit which opens in the side surface of the incubator, and each chemical analysis film is incubated in the cell and the optical density of the color formed by the coloring reaction is optically measured with the chemical analysis film held in the cell.

As described above, the chemical components to be analyzed with the chemical analysis film include various components such as urea nitrogen, glucose, hemoglobin, ammonia and the like, and different types of chemical analysis film are used for different chemical components.

Depending on the kind of chemical component, gas generated from one chemical analysis film can adversely affect measurement on the chemical analysis film subsequently inserted into the cell when it is inserted immediately after the preceding chemical analysis film is discharged from the cell. For example, when one chemical analysis film is for urea nitrogen and the next chemical analysis film is for ammonia, ammonia gas generated from the chemical analysis film for urea nitrogen remains in the cell and affects the result of measurement on the next chemical analysis film for ammonia.

In order to overcome such a problem, it has been proposed to insert the next chemical analysis slide a predetermined time (about 1 to about 30 seconds) after discharge of the preceding chemical analysis slide. (European Patent Publication No. 365006)

In the system disclosed in Japanese Unexamined Patent Publication No. 2(1990)-247563, a plurality of chemical analysis films for the same analyte are connected to a tape in a continuous length, and the interfering substances are variously dealt with during measurement on one chemical analysis film or between discharge of one chemical analysis film from the cell and insertion of the next chemical analysis film into the cell.

However, the method disclosed in European Patent Publication No. 365006 is disadvantageous in that a predetermined time interval is required between the measurements, which prevents shortening of the time required for the biochemical analysis.

In Japanese Unexamined Patent Publication No. 2(1990)-247563, there is neither description nor suggestion on the case where the chemical analysis film which generates the interfering substances and that affected by the interfering substances are for different analytes. Further though the chemical analysis film in a continuous length is easy to manufacture, it makes it difficult to miniaturize the analysis apparatus. The present invention is directed to a system in which discrete chemical analysis films (those in the form of a slide with frame or in the form of a chip) are used.

SUMMARY OF THE INVENTION

In view of the foregoing observations and description, the primary object of the present invention is to provide a method of biochemical analysis using discrete chemical analysis films in which gas or the like generated from one chemical analysis film is prevented from affecting the measurement on the next chemical analysis film without elongating the time required for the biochemical analysis irrespective of whether the chemical analysis films for the same analytes or different analytes are successively measured.

The method of the present invention is characterized in that when a chemical analysis film generates gas or the like which affects the accuracy of the measurement on a subsequently measured chemical analysis film, a film deposited with aqueous sample liquid, water or aqueous liquid which adsorbs the gas or the like is inserted into the cell of the incubator after discharge of the former chemical analysis film before the latter chemical analysis film.

That is, in accordance with the present invention, there is provided a method of biochemical analysis wherein a dry chemical analysis film deposited with a sample liquid is inserted into an incubator to be incubated at a predetermined temperature, a coloring reaction of the chemical analysis film is measured after the incubation and then the chemical analysis film is discharged from the incubator, a plurality of chemical analysis films being subjected to these steps one by one after the preceding chemical analysis film is discharged from the incubator, the method characterized in that when a first chemical analysis film is for an analyte which generates an interfering gas or the like which can adversely affects the accuracy of measurement of other chemical analysis films and a second chemical analysis film the accuracy of measurement on which can be adversely affected by the interfering gas or the like is to be inserted into the incubator after the first chemical analysis film is discharged, an adsorptive film which adsorbs the interfering gas or the like generated from the first chemical analysis film is inserted into the incubator after discharge of the first chemical analysis film prior to insertion of the second chemical analysis film.

As the adsorptive film, a dry chemical analysis film which is for an analyte the accuracy of measurement of which cannot be adversely affected by the interfering gas or the like generated from the first chemical analysis film and is deposited with an aqueous sample liquid may be used, or a dummy chemical analysis film deposited with water or an aqueous liquid which need not be analyzed.

In the case where a dummy chemical analysis film is used as the adsorptive film, the step of measuring the coloring reaction may be carried out though not necessary.

Insertion and discharge of the adsorptive film into and from the incubator may be repeated a plurality of times so that the interfering gas or the like generated from the first chemical analysis film can be more surely removed from the incubator.

In accordance with the method of the present invention, the interfering gas or the like generated from the first chemical analysis film is removed from the incubator by the water component of the adsorptive film prior to insertion of the second chemical analysis film, and accordingly, the accuracy of measurement on the second chemical analysis film cannot be affected by the interfering gas or the like.

Further since the interfering gas or the like is removed from the incubator by adsorption by the adsorptive film, the interfering gas or the like can be quickly and surely removed from the incubator as compared with when it is removed by free diffusion and accordingly, the interval between the measurements on the first chemical analysis film and the second chemical analysis film may be short, whereby the time required for the biochemical analysis can be shortened.

When a dry chemical analysis film which is for an analyte the accuracy of measurement of which cannot be adversely affected by the interfering gas or the like generated from the first chemical analysis film and is deposited with an aqueous sample liquid is used as the adsorptive film, the interfering gas or the like can be adsorbed without interrupting the measurement, whereby the time required for the biochemical analysis can be further shortened.

Further in accordance with the method of the present invention, since the discrete chemical analysis films each of which is for one sample liquid are used, the chemical analysis film to be inserted into the incubator after one chemical analysis film may be either for the same analyte as said one chemical analysis film or for a different analyte.

DESCRIPTION OF THE PREFERRED EMBODIMENT

Figure 2:
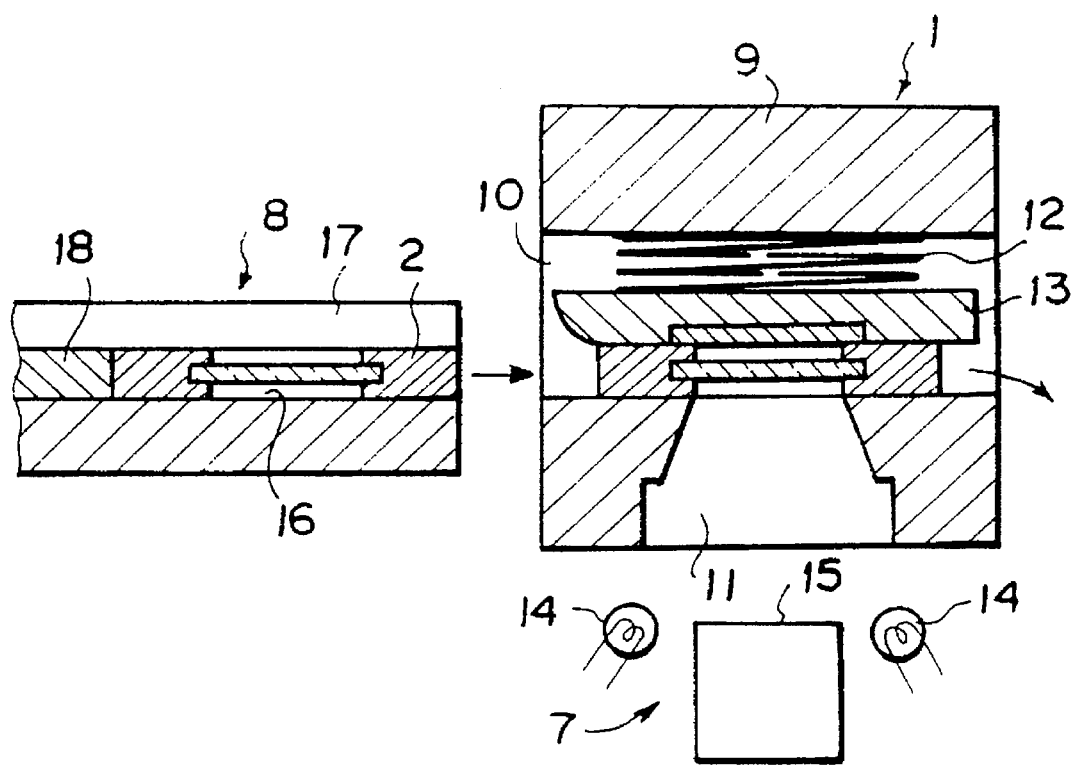
FIG. 2 is a fragmentary cross-sectional view showing a part of an apparatus for carrying out the method of the embodiment.
Figure 3:
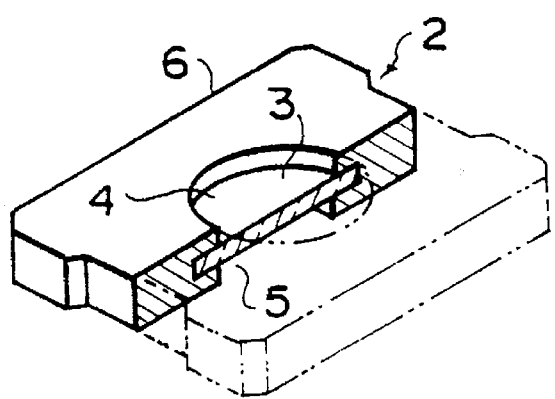
FIG. 3 is a perspective view partly in cross-section showing an example of a dry chemical analysis film which is employed in the present invention.

As shown in FIG. 2, an apparatus for carrying out a method of biochemical analysis in accordance with an embodiment of the present invention includes an incubator 1 comprising an incubator body 9 having therein a heater (not shown). A cell 10 in the form of a slit horizontally extending through the incubator body 9 from one side to the other is provided in the incubator body 9. A light measuring window 11 is formed in the bottom of the incubator body 9 to open to the cell 10. In this particular embodiment, chemical analysis slides 2 such as shown in FIG. 3 is used and is inserted into the cell 10. A slide pressing member 13 for pressing the chemical analysis slide 2 against the bottom surface of the cell 10 is provided in the cell 10 and is urged toward the light measuring window 11 under the force of a spring 12. The slide pressing member 13 is formed, for instance, of plastic. The inner surface of the cell 10 and the surface of the slide pressing member 13 opposed to the slide 2 are coated with polytetrafluoroethylene not to absorb or adsorb gases generated from the slide 2.

A light measuring system 7 comprising a light source 14 for projecting light onto the slide 2 in the cell 10 and a photodetector 15 for measuring reflected light from the slide 2 is provided below the light measuring window 11.

A slide inserting mechanism 8 inserts the slide 2 into the cell 10 in a predetermined position and discharges the same therefrom. The slide inserting mechanism 8 comprises a sliding surface 16 substantially on the same level with the bottom surface of the cell 10, a guide 17 for guiding the slide 2 and a lever 18 for pushing the slide 2.

As shown in FIG. 3, the chemical analysis slide 2 comprises a dry chemical analysis film chip 3 and a frame member 6 which supports the film chip 3. In this particular embodiment, the film chip 3 comprises a transparent support sheet and a reagent layer, a reflective layer and a spreading layer formed on the support sheet in this order. The frame member 6 is provided with an opening 4 through which a sample liquid is spotted on the film chip 3 and with an opening 5 through which the coloring reaction is measured.

When a sample liquid is analyzed with such a slide 2, the sample liquid spotted on the film chip 3 through the opening 4 and is incubated, for instance, at 37° C. for six minutes to promotes coloring reaction between the sample liquid and the reagent on the slide 2. Then light is projected on the film chip 3 through the opening 5 and an analyte in the sample liquid is quantitatively analyzed on the basis of the reflected light from the slide 2 (colorimetry).

A method of biochemical analysis in accordance with an embodiment of the present invention will be described with reference to FIGS. 1A to 1F, hereinbelow.

Figure 1A:
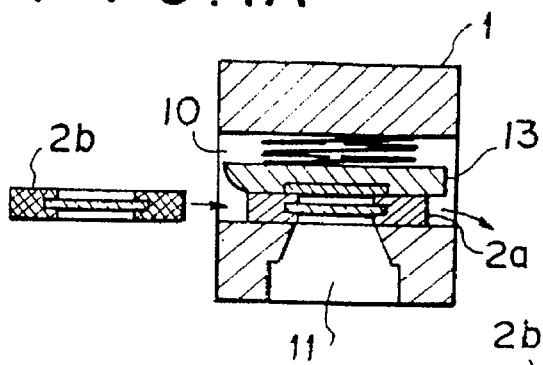
FIGS. 1A to 1F are schematic views for illustrating a method of biochemical analysis in accordance with an embodiment of the present invention.

As shown in FIG. 1A, a first chemical analysis slide 2a is first inserted into the cell 10 of the incubator 1 and the coloring reaction on the first chemical analysis slide 2a is measured. When the first chemical analysis slide 2a is for determining TP (total protein) or BUN (blood urea N), NH$_3$ gas is generated during determination and stays in the cell 10 for a long time.

When a second chemical analysis slide 2c for determining BUN, NH$_3$ or CRE (creatinine) is inserted into the cell 10, measurement on the second chemical analysis slide 2c can be affected by the residual NH$_3$ gas. That is, since the determination of BUN, NH$_3$ or CRE is made on the basis of the amount of NH$_3$ gas generated in the reagent layer, the result of the determination is increased by the amount of the residual NH$_3$ gas.

In this embodiment, when a chemical analysis slide for determining BUN, NH$_3$ or CRE (creatinine) is to be measured after the chemical analysis slide for determining TP or BUN, a chemical analysis slide 2b which absorbs NH$_3$ gas and measurement on which cannot be affected by NH$_3$ gas (e.g., a chemical analysis slide which is for quantifying calcium and has a spreading layer impregnated with acid such as citric acid; disclosed for instance in U.S. Pat. Nos. 4,871,679 and 4,966,784) is inserted into the cell 10 before the second chemical analysis slide 2c is inserted into the cell 10.

Figure 1B:
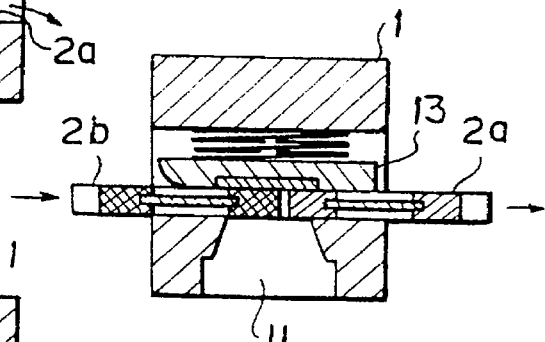
Figure 1C:
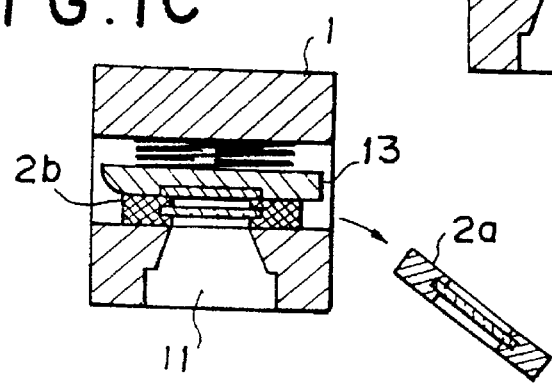

That is, in the state where the first chemical analysis slide 2a is in the cell 10, the adsorptive chemical analysis slide 2b is transferred near the cell 10 as shown in FIG. 1A, and then the adsorptive chemical analysis slide 2b is inserted into the cell 10 as shown in FIG. 1B. Thus the first chemical analysis slide 2a is pushed out of the cell 10 by the adsorptive chemical analysis slide 2b as shown in FIG. 1C.

While the adsorptive chemical analysis slide 2b is incubated and measured in the cell 10, the residual NH$_3$ gas is absorbed by the slide 2b. More particularly, the residual NH$_3$ gas is absorbed in water contained in the film chip 3 of the adsorptive chemical analysis slide 2b.

Figure 1D:
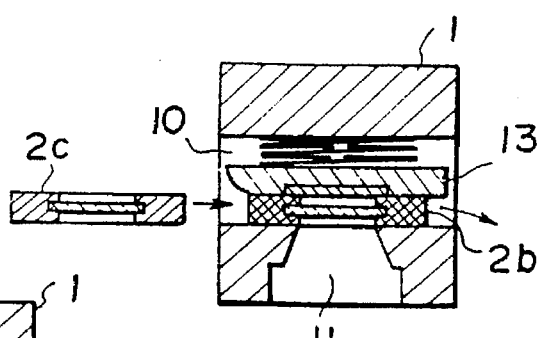
Figure 1E:
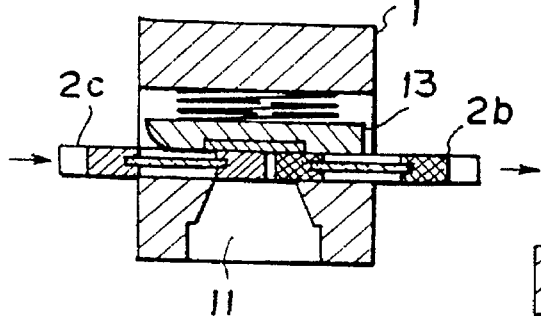
Figure 1F:
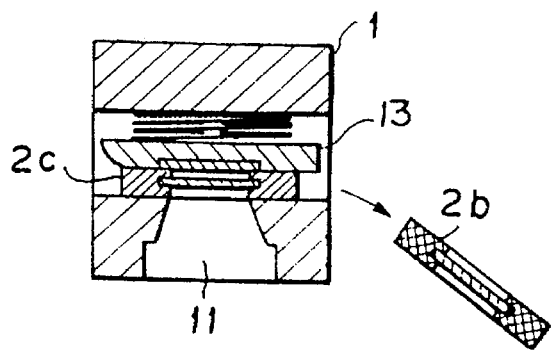

When measurement on the adsorptive chemical analysis slide 2b is finished, the second chemical analysis slide 2c is inserted into the cell 10 pushing the adsorptive chemical analysis slide 2b out of the cell 10 as shown in FIGS. 1D to 1F. Thus the second chemical analysis slide 2c can be measured in the cell 10 free from the residual NH$_3$ gas, and BUN, NH$_3$ or CRE can be quantitatively analyzed with a high accuracy.

Examples 1 to 4 were carried out in accordance with the method of this embodiment. In each example, a chemical analysis slide for determining TP was used as the first chemical analysis slide 2a and a chemical analysis slide for determining NH$_3$ was used as the second chemical analysis slide 2c . As the adsorptive chemical analysis slide 2b, chemical analysis slides for GLU (glucose), TBIL (total bilirubin), UA (urea acid) and ALP (alkaline phosphatase) were used in examples 1 to 4, respectively. As the biochemical analysis apparatus, FDC 5500 Analyzer (a chemical analysis apparatus for clinical examination system manufactured by Fuji Photo Film Co. Ltd) was used and an imitation solution of blood serum containing therein a predetermined concentration of NH$_3$ was used as the sample liquid. As a control, measurement on the second chemical analysis slide 2c was taken without inserting any adsorptive chemical analysis slide. Results of the examples and the control are shown in the following table. In the table, the actual NH$_3$ concentration represents a value obtained by spotting the same sample liquid as used in each of the embodiments and the control on a chemical analysis slide for NH$_3$, measuring the optical density after incubation and determining the concentration of NH$_3$ on the basis of the optical density.

|  | 1st slide | adsorptive slide | 2nd slide | actual NH$_3$ concentration | | measured NH$_3$ concentration | | error | |
| --- | --- | --- | --- | --- | --- | --- | --- | --- | --- |
| ex. 1 | TP | GLU | NH$_3$ | concentration OD | 59 μg/dl 0.326 | concentration OD | 60 μg/dl 0.329 | concentration OD | +1% +0.003 |
| ex. 2 | TP | TBIL | NH$_3$ | concentration OD | 54 μg/dl 0.316 | concentration OD | 54 μg/dl 0.316 | concentration OD | 0 0 |
| ex. 3 | TP | UA | NH$_3$ | concentration OD | 55 μg/dl 0.316 | concentration OD | 57 μg/dl 0.322 | concentration OD | +2% +0.006 |
| ex. 4 | TP | ALP | NH$_3$ | concentration OD | 55 μg/dl 0.318 | concentration OD | 60 μg/dl 0.328 | concentration OD | +5% +0.010 |
| control | TP |  | NH$_3$ | concentration OD | 63 μg/dl 0.334 | concentration OD | 80 μg/dl 0.370 | concentration OD | +17% +0.036 |

As can be understood from the table, the accuracy of measurement on the second chemical analysis slide 2a can be held excellent.

As the adsorptive chemical analysis slide 2b, a dummy chemical analysis slide spotted with water instead of sample liquid may be used. As a dummy slide, instead of a chemical analysis slide having a chemical analysis film chip 3, those formed by forming a hydrophilic polymer layer such as of gelatin on a base film and laminating thereon a member such as fabrics, filter paper or membrane filter which is porous and can hold water (equivalent to a dry chemical analysis film chip without reagent layer), or a member such as fabrics, filter paper or the like which has a rigidity enough to be handled by the biochemical analysis apparatus to be used and can hold water can be used.

Though, in the embodiment described above, the present invention is applied to the case where the interfering gas or the like is NH$_3$ gas, the present invention can be applied to various interfering gas or the like. For example, the first chemical analysis slide 2a may be one for determining inorganic phosphorous which generates SO$_2$ gas with the second chemical analysis slide 2c being one for determining CKMB (creatine kinase MB) the accuracy of measurement on which is affected by SO$_2$ gas.

The present invention need not be limited to the embodiment described above. For example, various other analyzers can be used as the biochemical analysis apparatus. Further though, in the embodiment described above, a chemical analysis slide is used as the chemical analysis film, a frameless chemical analysis film (a film chip) can also be used.

Even if a chemical analysis film which is not affected by the interfering gas or the like though not adsorbing the interfering gas or the like is used in place of the adsorptive film, an effect similar to that obtained by the method of the present invention can be obtained.

Further, an effect similar to that obtained by the method of the present invention can be obtained also by inserting the chemical analysis film which is affected by the interfering gas or the like into a cell different from that into which the chemical analysis film generating the interfering gas or the like was inserted.

Thus, in accordance with the present invention, when a chemical analysis film generates interfering gas or the like which affects the accuracy of the measurement on a subsequently measured chemical analysis film, an adsorptive film deposited with aqueous sample liquid, water or aqueous liquid which adsorbs the gas or the like is inserted into the cell of the incubator after discharge of the former chemical analysis film before the latter chemical analysis film and the interfering gas or the like is adsorbed and removed by the water on the adsorptive film. Accordingly the measurement on the subsequently measured chemical analysis film can be taken without affected by the interfering gas or the like, whereby the accuracy of measurement can be ensured.

Further since the interfering gas or the like is removed from the incubator by adsorption by the adsorptive film, the interfering gas or the like can be efficiently removed from the incubator, the throughput speed of biochemical analysis is hardly lowered. When a dry chemical analysis film which is for an analyte the accuracy of measurement of which cannot be adversely affected by the interfering gas or the like generated from the first chemical analysis film and is deposited with an aqueous sample liquid is used as the adsorptive film, the interfering gas or the like can be adsorbed without interrupting the measurement, whereby the time required for the biochemical analysis can be further shortened.

What is claimed is:

1. In a method for biochemical analysis wherein each one of a plurality of dry chemical analysis films having a liquid sample for analysis of different analytes thereon is sequentially inserted into an incubator, sequentially incubated at a predetermined temperature to cause a coloring reaction to take place, and an extent of the coloring reaction is measured after the incubation and the sequence of such incubation is carried out so that each preceding chemical analysis film is discharged from the incubator prior to insertion of the next chemical analysis film to be analyzed, the improvement which comprises controlling the sequence of the insertion and discharge of each of said plurality of chemical analysis films so that the accuracy of measurement for the second through last of the plurality of chemical analysis films is not adversely affected by the analysis of the next preceding chemical analysis film, wherein a first chemical analysis film having a first analyte for analysis thereon is used which generates a gas which can adversely affect the accuracy of the analysis of other different analytes and a second chemical analysis film having a second analyte thereon for analysis is used, the accuracy of measurement of which is adversely affected by the gas generated by the first analyte, and wherein after discharge of the first chemical analysis film, a third chemical analysis film having a third analyte thereon for analysis and having adsorbability to adsorb said gas, the accuracy of the analysis of which is not adversely affected by the gas generated by the first analyte is inserted and analyzed prior to insertion of the second chemical analysis film.

2. In a method for biochemical analysis wherein each one of a plurality of dry chemical analysis films having a liquid sample for analysis thereon are sequentially inserted into an incubator, sequentially incubated at a predetermined temperature to cause a coloring reaction to take place, and an extent of the coloring reaction is measured after the incubation and the sequence of such incubation is carried out so that each preceding chemical analysis film is discharged from the incubator prior to insertion of the next chemical analysis film to be analyzed, the improvement which comprises a first chemical analysis film having a first analyte thereon for analysis being used which generates a gas which can adversely affect the accuracy of the analysis of other analytes, and a second chemical analysis film having a second analyte thereon for analysis being used, the accuracy of measurement of which is adversely affected by the gas generated by the first analyte, and wherein after discharge of the first chemical analysis film, a third dummy film having water thereon is inserted into the incubator prior to insertion of the second chemical analysis film.

* * * * *